(12) United States Patent
Kanaly

(10) Patent No.: US 12,226,131 B2
(45) Date of Patent: Feb. 18, 2025

(54) SPINAL FIXATION TOOL, SYSTEM AND METHOD

(71) Applicant: Charles Kanaly, Mattapoisett, MA (US)

(72) Inventor: Charles Kanaly, Mattapoisett, MA (US)

( * ) Notice: Subject to any disclaimer, the term of this patent is extended or adjusted under 35 U.S.C. 154(b) by 0 days.

(21) Appl. No.: 18/696,965

(22) PCT Filed: Oct. 17, 2022

(86) PCT No.: PCT/US2022/078196
§ 371 (c)(1),
(2) Date: Mar. 28, 2024

(87) PCT Pub. No.: WO2023/069890
PCT Pub. Date: Apr. 27, 2023

(65) Prior Publication Data
US 2024/0261001 A1    Aug. 8, 2024

Related U.S. Application Data

(60) Provisional application No. 63/256,727, filed on Oct. 18, 2021.

(51) Int. Cl.
*A61B 17/70*    (2006.01)
*A61B 17/00*    (2006.01)

(52) U.S. Cl.
CPC ...... *A61B 17/7083* (2013.01); *A61B 2017/00407* (2013.01)

(58) Field of Classification Search
CPC ............ A61B 17/7083; A61B 17/7085; A61B 17/7089
See application file for complete search history.

(56) References Cited

U.S. PATENT DOCUMENTS

| 8,211,145 B2 | 7/2012 | Dalton |
| 8,568,451 B2 | 10/2013 | Zucherman et al. |

(Continued)

FOREIGN PATENT DOCUMENTS

| EP | 2737866 A1 | 6/2014 |
| EP | 3659525 A1 | 6/2020 |
| WO | 2021118454 A1 | 6/2021 |

OTHER PUBLICATIONS

"International Search Report and Written Opinion Received for PCT Patent Application No. PCT/US2022/078196, mailed on Jan. 11, 2023", 8 pages.

*Primary Examiner* — Ellen C Hammond
(74) *Attorney, Agent, or Firm* — Adler Pollock & Sheehan P.C.

(57) ABSTRACT

A spine fixation tool and system for use with rods and screws. The system includes a rod holder/inserter having a rod guide member and a swivel arm pivotably connected to the guide member. The swivel arm is configured to secure and retain the rod therein, and move relative to the rod guide member to position the rod in screws within a patient's vertebrae during spinal surgery. The system further includes an inner stylet that retains the rod and an outer sheath configured to engage the inner stylet. The system is used to insert a rod through screws placed in a patient's vertebrae. With swivel arm secured on top of heads of the screws. A surgeon uses spinal navigation system to help position the rod. The system enables minimally invasive spinal fixation surgery with smaller and fewer skin incisions.

20 Claims, 5 Drawing Sheets

(56) References Cited

U.S. PATENT DOCUMENTS

| | | | |
|---|---|---|---|
| 9,532,815 B2 | 1/2017 | Jackson | |
| 10,568,677 B2 | 2/2020 | Divincenzo et al. | |
| 2003/0225408 A1* | 12/2003 | Nichols | A61B 17/7083 606/256 |
| 2007/0191846 A1* | 8/2007 | Bruneau | A61B 17/7008 606/86 A |
| 2011/0184464 A1* | 7/2011 | Fiorella | A61B 17/7089 606/264 |
| 2014/0249592 A1* | 9/2014 | Black | A61B 17/7089 606/86 A |
| 2015/0066042 A1 | 3/2015 | Cummins et al. | |
| 2017/0056076 A1* | 3/2017 | Kim | A61B 17/7089 |
| 2019/0125416 A1* | 5/2019 | Abe | A61B 17/7034 |
| 2021/0393296 A1* | 12/2021 | Triplett | A61B 17/7083 |
| 2022/0240986 A1 | 8/2022 | Scholl | |

* cited by examiner

SPINAL FIXATION TOOL, SYSTEM AND METHOD

CROSS REFERENCE TO RELATED APPLICATION

This application is a National Phase filing under 35 U.S.C § 371 of International Application No. PCT/US2022/078196 filed Oct. 17, 2022, which claims the benefit of priority to U.S. Provisional Patent Application No. 63/256,727, filed Oct. 18, 2021, each of which is incorporated by reference herein in their entirety.

BACKGROUND

The present invention relates generally to spinal fixation surgery, and more specifically to a spinal fixation tool and system.

In general, spinal fusion is surgery to permanently connect two or more vertebrae in a spine, eliminating motion between them. Typically, spinal fusion involves techniques designed to mimic a normal healing process of broken bones. During spinal fusion, a surgeon places bone or a bone-like material within the space between two spinal vertebrae. Metal plates, screws and rods may be used to hold the vertebrae together, so they can heal into one solid unit.

SUMMARY

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In one aspect, the invention includes a device including a rod holder having at least one centrally located external fixation point for a rod holder navigation tracker, a swivel arm having at least one upper located external fixation point for a swivel arm navigation tracker, the swivel arm pivotally attached to the rod holder, an inner stylet, a bottom portion of the inner stylet comprising a pincher to receive a rod, an outer sheath, the outer sheath configured to slid over the inner stylet, a T depressor configured to slide over an upper portion of the inner sytlet, and a ratchet positioned on a top portion of the swivel arm configured to lock on to the T depressor.

In another aspect, the invention includes a spine fixation system comprising a rod holder/inserter including a rod guide member and a swivel arm pivotably connected to the rod guide member, wherein the rod guide member includes an opening dimensioned to receive the swivel arm therethrough, a distal end having an open back to receive a rod therethrough, and wherein the swivel arm includes a distal front opening dimensioned to receive the rod and having a solid distal base and back wall to secure the rod. The system further comprises an inner stylet including a pincher at its distal end having an opening configured to receive and retain the rod therein, a U-shaped T depressor including two arms defining an insertion groove therebetween and each having a beveled edge configured to lock into a portion of the swivel arm; and an outer sheath including a lower part and an upper part configured to cooperates with the lower part, the outer sheath including means for engaging the inner stylet.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

These and other features, aspects, and advantages of the present invention will become better understood with reference to the following description, appended claims, and accompanying drawings where:

DETAILED DESCRIPTION

Definitions

Figure 1:
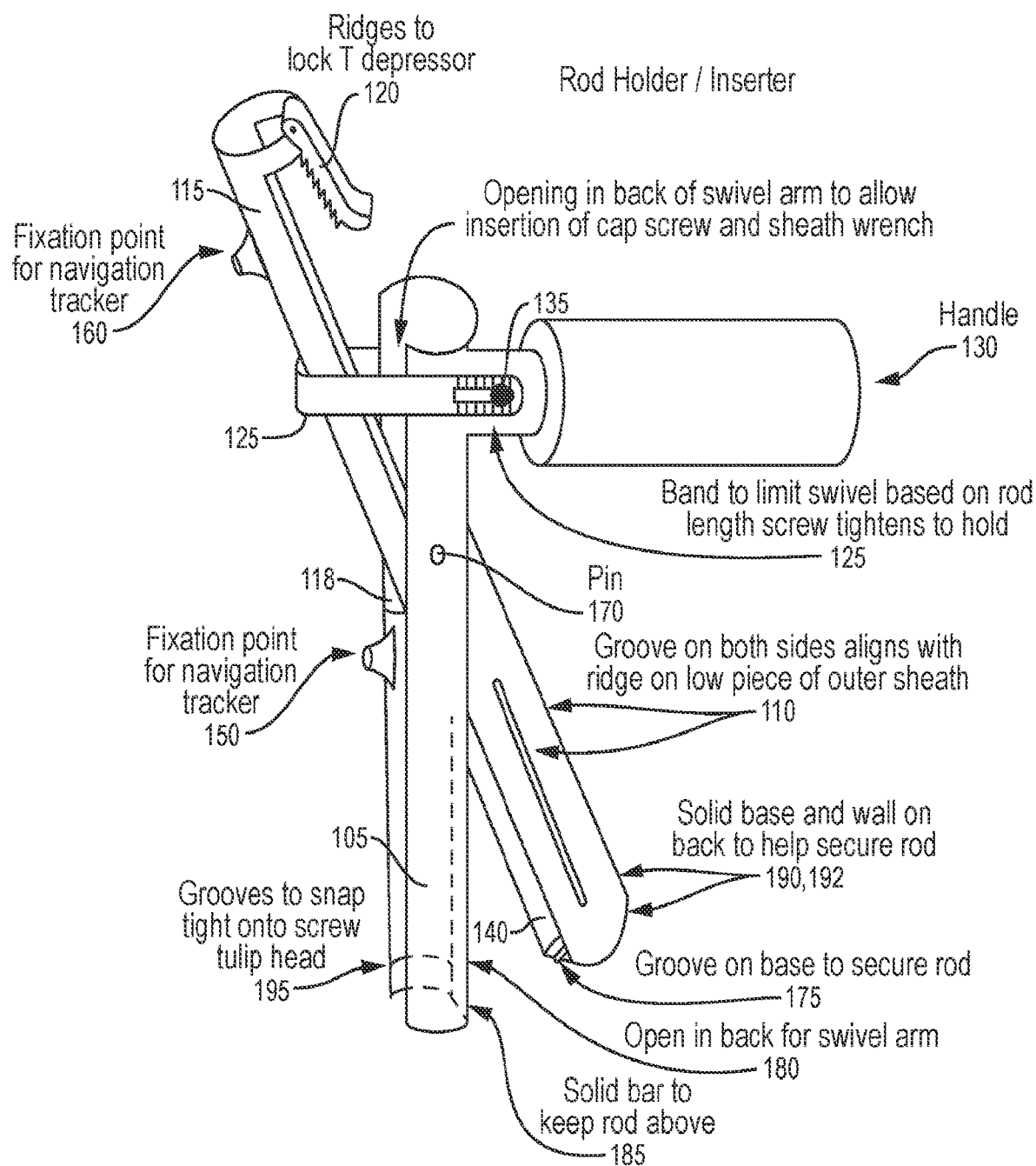
FIG. 1 illustrates an exemplary rod holder/inserter according to an embodiment of the present invention.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

Spinal Fixation Tool, System and Method

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

Current spinal fixation surgical techniques require either a large open surgery with direct visualization of the implanted hardware, or minimally invasive methods where each screw head has an extension connector that controls the screw head and extends up through the skin surface. This extension connector allows the surgeon direct control of every screw head from the skin surface. Further advances in spine surgery with spinal navigation and robotics have made possible computerized planning of implant insertion and placement, the tracking of surgical instruments on a computer screen, and also guidance of and assistance with implant insertion.

The present invention advances minimally invasive spine surgery by allowing for the planning, tracking, and guidance of rod insertion using spinal navigation equipment.

The present invention also removes the requirement for the screw percutaneous extension connectors/control towers that previously would have extended through the skin surface. Current methods utilizing extension connectors require larger percutaneous skin incisions so that the size of the tower is accommodated as well as the need to fit the inserted rod. Current methods also require enough skin opening for every screw to have an extension connector protruding through the skin at the same time. The present invention permits smaller skin incisions since screw head extension connectors are no longer required and multiple screws can be inserted through the same incision. The present invention can be used throughout the entire thoracolumbar spinal fusion market.

Briefly, the screws are planned on the navigation software and inserted according to the plans and current minimally invasive techniques. A rod is also planned on the navigation software to easily align with all of the screw heads. The rod length is measured on the planning software. The surgeon briefly places screw tulip head-turners down on each screw to ensure the screw head tulips are aligned to easily accept an inserted rod.

The components and assembly of an exemplary spine fixation device, or system, 500 according to the present invention are illustrated in FIGS. 1-7 and described below.

Figure 5:
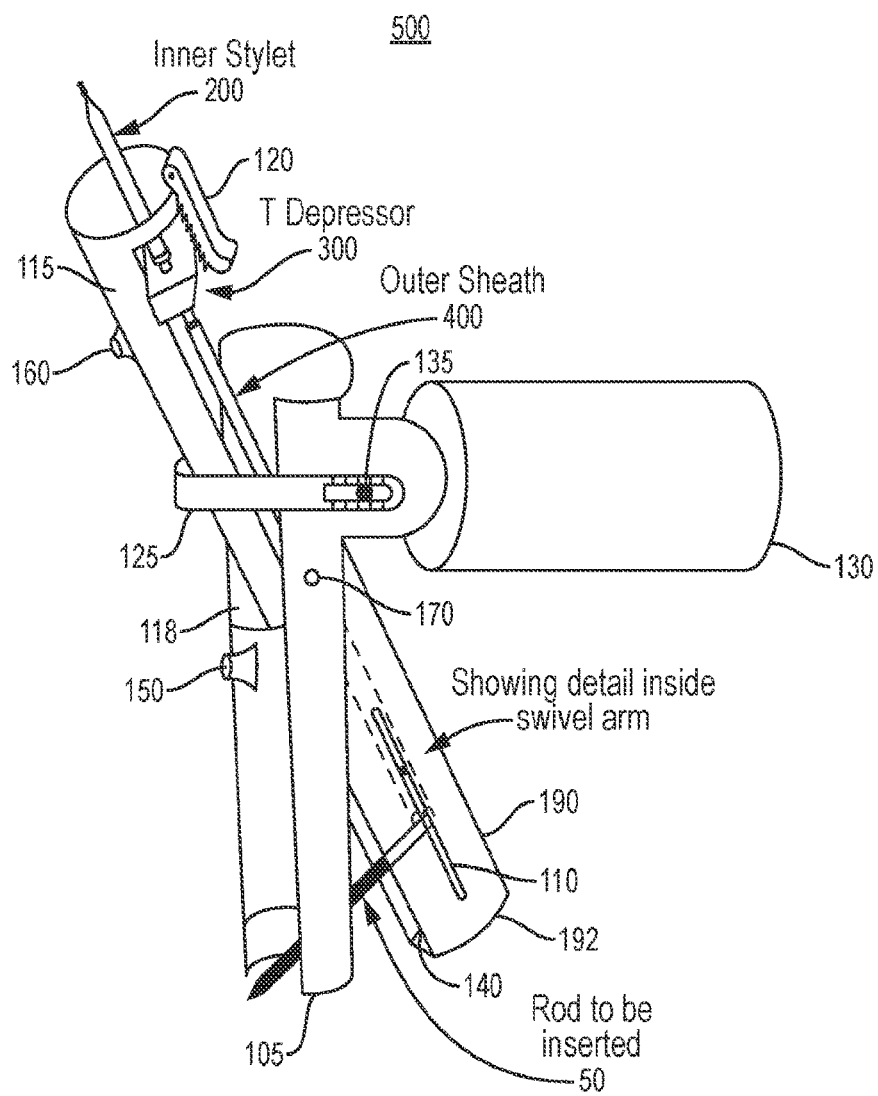
FIG. 5 illustrates an exemplary assembled spinal fixation system according to an embodiment of the present invention.
Figure 6:
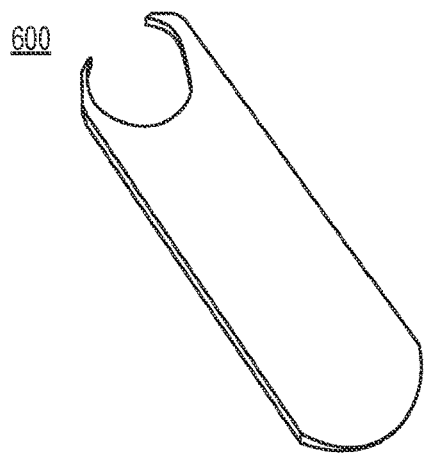
FIG. 6 illustrates an exemplary sheath locking wrench according to an embodiment of the present invention.
Figure 7:
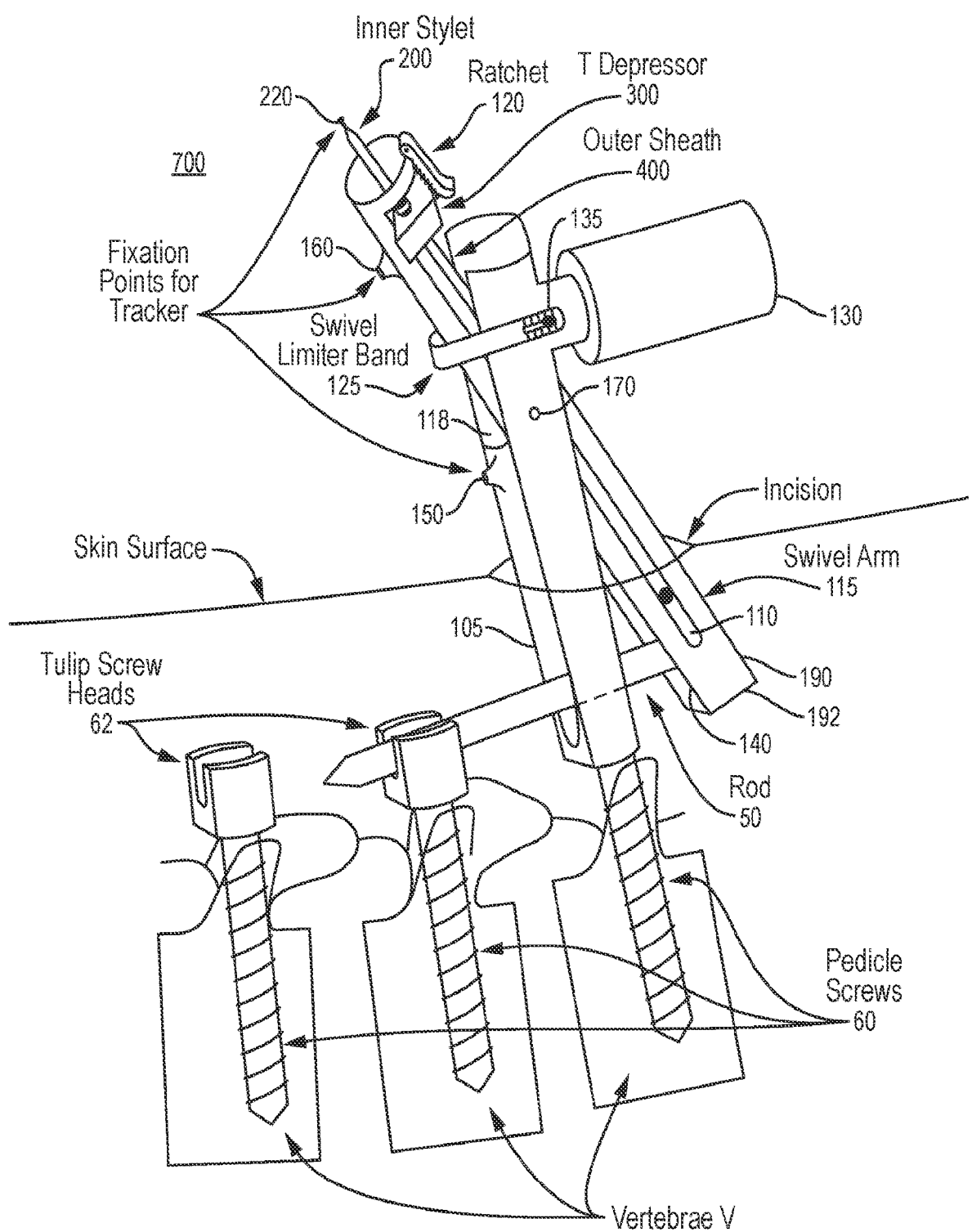
FIG. 7 illustrates an exemplary surgical method for using the spinal fixation system of FIG. 5 in connection with a patient's spine.

A rod holder/inserter 100 of the system 500 (also referred to the "tool") according to an embodiment of the present invention is shown in FIGS. 1, 5 and 7. The tool 100 includes a rod holder, or guide member, 105 and a swivel arm 115 pivotably connected to the rod guide member 105, e.g., by a pin 170. The rod guide member 105 includes an opening 118 that is dimensioned to receive the swivel arm 115 therethrough, and a band 125 configured to limit swiveling motion of the swivel arm 115 based on a rod's length. The 125 band includes a screw 135 to tighten a position of the swivel arm 115 with respect to the rod guide member 105. The rod guide member 105 also includes a handle 130 that engages the band 125 in some embodiments, and at least one external fixation point 150 (e.g., centrally located on the rod guide member 105) for a rod guide member navigation tracker. The distal end of the rod guide member 105 includes an open back to receive the rod 50 therethrough, a solid bar 185 that is configured to support the rod 50 thereon, and grooves 195 to engage (i.e., snap tightly onto) the screw tulip heads 62.

The swivel arm 115 includes a ratchet 120 and at least one external fixation point 160 for a swivel arm navigation tracker at its top, or proximal end, and distal grooves 110, as further discussed below. The swivel arm 115 further includes a distal front opening 140 dimensioned to receive the rod 50 and having a groove 175 to secure the rod 50 therein, and a solid distal base 190 and back wall 192 to further secure the rod 50.

Figure 2:
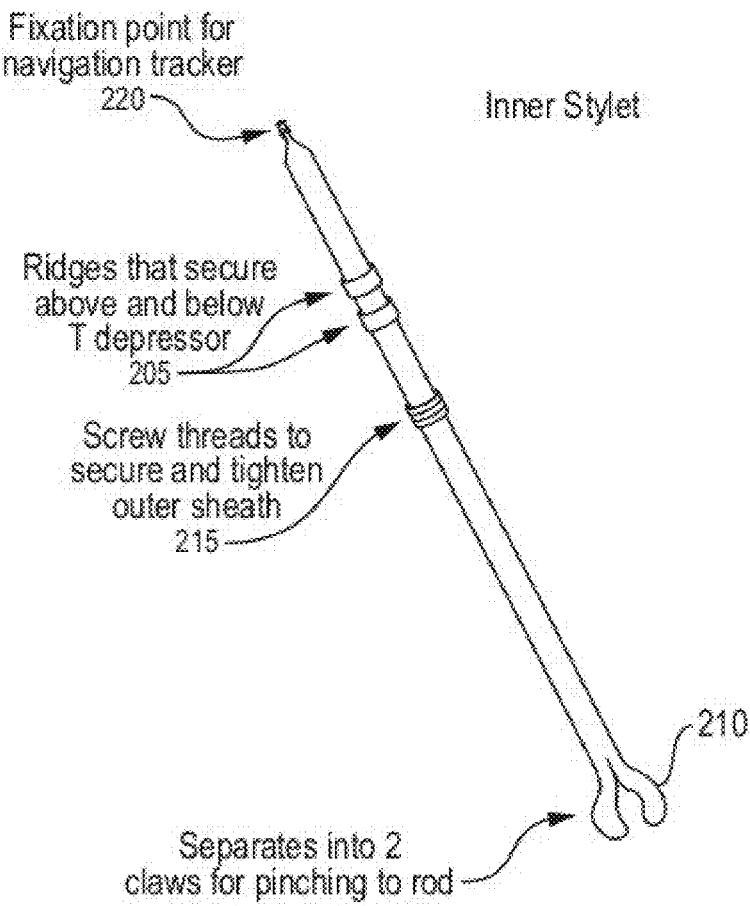
FIG. 2 illustrates an exemplary inner stylet according to an embodiment of the present invention.

An inner stylet 200 of the system 500 according to an embodiment of the present invention is shown in FIG. 2 and includes a pincher 210 at its distal end having an opening configured to receive and retain the rod 50 therein, and an inner stylet navigation tracker 220 at its proximal (i.e., top) end. This tracker 220 is shown as having a spherical/ball shape, but may have other configurations in alternate embodiments of the system 500. The inner stylet 200 also includes ridges 205 and threads 215 between its proximal and distal ends, as further discussed below.

Figure 3:
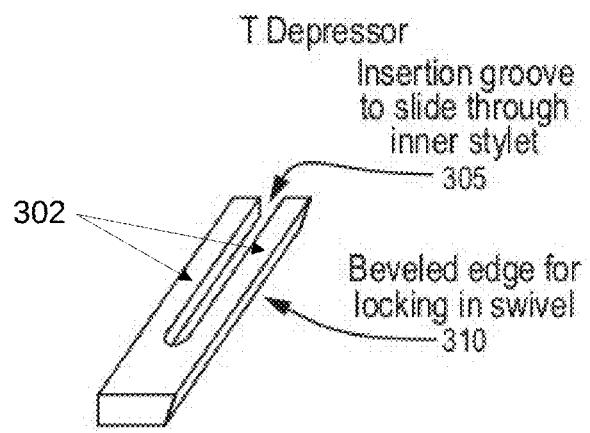
FIG. 3 illustrates an exemplary T depressor according to an embodiment of the present invention.

A U-shaped T depressor 300 of the system 500 according to an embodiment of the present invention is shown in FIG. 3 and includes two arms 302 defining an insertion groove 305 therebetween. The insertion groove 305 is configured to engage the inner stylet 200 therein upon assembly of the system 500. The arms 302 each include a beveled edge 310 configured to lock into a portion of the swivel arm 115 upon assembly of the system 500. Further, the ratchet 120 of the swivel arm is configured to lock on to the T depressor 300 to facilitate moving same.

Figure 4:
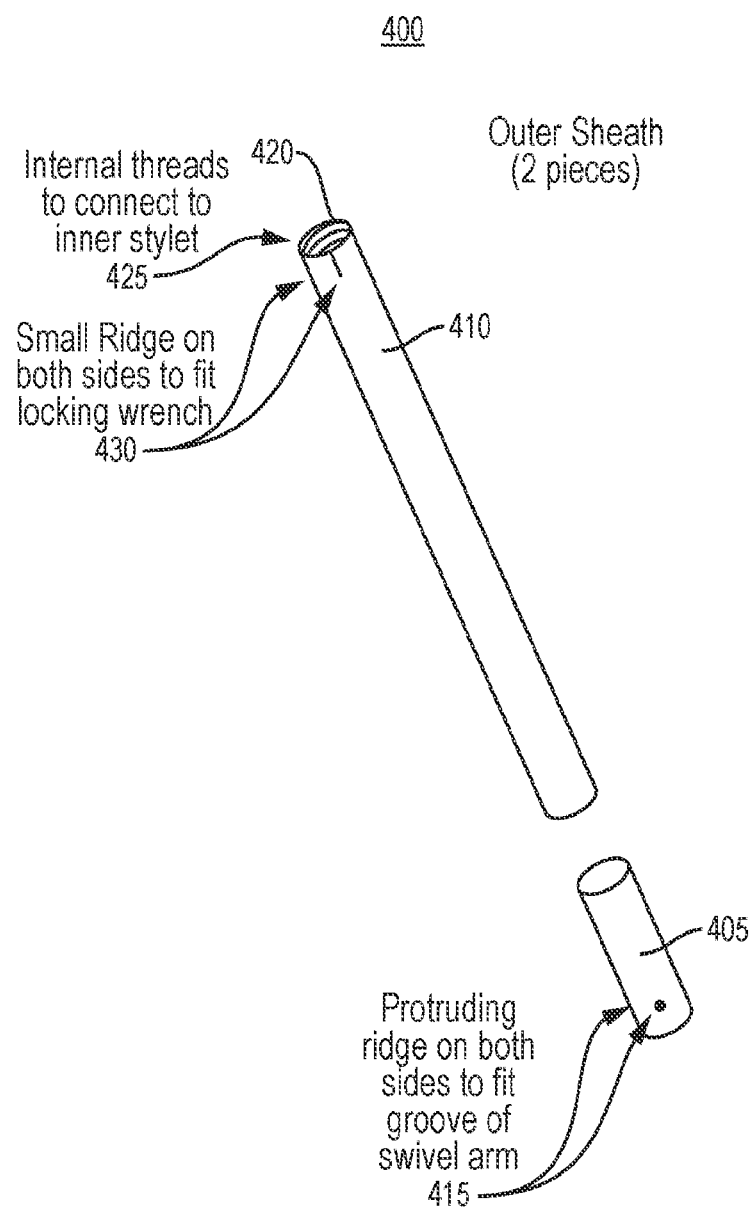
FIG. 4 illustrates an exemplary outer sheath according to an embodiment of the present invention.

An outer sheath 400 of the system 500 according to an embodiment of the present invention is shown in FIG. 4 and includes a lower (distal) part 405 and an upper (proximal) part 410 that cooperates with the lower part 405. The lower part 405 includes ridges 415 that protrude from both sides and are configured to insertably engage the distal grooves 110 of the swivel arm 115. The upper part 410 includes an open proximal end 420 having internal threads 425 that are configured to engage the threads 215 on the inner stylet 200 and a small ridge 430 configured to engage a locking wrench 600, as discussed below.

Using navigation software, an appropriately-sized rod 50 is selected to engage tulip screw heads 62 of screws 60 placed into a patient's vertebrae V (see FIG. 7). According to embodiments of the invention, and with reference to FIG. 5, the rod 50 is first placed into the opening of the pincher 210 of the inner stylet 200. The lower part 405 and upper part 410 of the outer sheath 400 are slid over the inner stylet 200, whereupon the threads 215 of the inner stylet 200 are screwed into the internal threads 425 of the outer sheath 400 to hold the inner stylet 200 and the rod 50 therein. The rod 50 needs to be placed straight out from (i.e., perpendicular to) the sheath 400. The sheath 400 is tightened with a sheath locking wrench 600 (see FIG. 6) that engages the ridges on the proximal end 420 of the sheath 400 to secure it to the inner stylet 200. As shown in FIGS. 5 and 7, the assembled sheath 400, stylet 200 and rod 50 are placed down into the swivel arm 115 at its proximal (top) end. The ridges 415 of the lower part 405 of the outer sheath 400 fit into the distal grooves 110 on the swivel arm 115. The surgeon positions the swivel arm 115 straight in the rod guide member 105, and advances the rod until it is at the tip of the distal end of the swivel arm 115. The T depressor 300 is then slid onto the stylet 200, locking it in position with the ratchet 120 on top of the swivel arm 115. The swivel arm limiter band 125 is then adjusted and the small screw 135 is tightened to the appropriate rod size. The limiter band 125 engages the handle 130, which is configured for the surgeon to manipulate the system 500 during use. The assembled system 500 (FIG. 5) is registered on the spinal navigation software (not shown), which registers the rod guide member navigation tracker (via the external fixation point 150), the swivel arm navigation tracker (via the external fixation point 160) and the inner stylet navigation tracker 220.

The use of the tool 100 to insert a rod 50 is illustrated in FIG. 7. First, all of the screws 60 are placed in the patient's vertebrae V with their respective tulip heads 62 exterior of the incision and skin surface, and the tool 100 is assembled and registered with the navigation software as described above. The tool 100 is placed through the skin incision onto a screw head 62 at either end of the construct (towards the head or foot). The swivel arm 115 of the tool 100 is snapped down securely on to the tulip head 62 of the screw 60. The surgeon looks at the spinal navigation computer screen (not shown) to ensure the tool 100 is in perfect alignment with the plan for placement of the rod 50. As shown, the rod 50 is held securely in that position. In an embodiment, the rod 50 can be locked in this position by incorporating a spinal robotic arm (not shown). It is also possible to allow the tool 100 to swivel/rotate while staying connected to the screw tulip head 62. The screw tulip head 62 is able to articulate in normal pedicle screws 60. This allows for the surgeon to rotate the rod 50 into place in the other adjacent screw heads. The T depressor 300 is pressed down (i.e., along the inner stylet 200 in a distal direction) which causes the rod 50 to swivel out of the distal end/base of the tool 100. The swivel arm 115 can also swivel in the rod holder 105 so that the rod 50 is not overextended from the rod holder too quickly. As the rod 50 is advanced, the swivel arm 115 can also swivel back and the navigation computer screen will show the rod 50 advancing. The rod 50 is kept advancing to the next screw head 62.

Once the T depressor 300 is completely depressed and the rod 50 is secured within all of the screw heads 62, a locking cap screw (not shown) is placed onto one of the screw heads. This can be performed through the front center of the rod holder on to that screw or a cap screw can also be placed on to a different screw based on surgeon preference. These cap screw inserters can also be tracked on the navigation software to help guide the surgeon for placement down to the screw heads 62. The surgeon inserts and locks as many cap screws as possible prior to removing the rod holder. After the rod 50 has been secured, the T depressor 300 is removed and then the outer sheath 400 is unscrewed using the sheath locking wrench 600 to release the grip on the rod 50. The outer sheath 400 and inner stylet 200 are then removed from the swivel arm 115. The rod holder 105 is then removed from the rod 50, and all caps screws are securely tighten onto the rod.

In summary, the present invention enables minimally invasive spinal fixation surgery that is not otherwise possible. Patients can have smaller skin incisions since the incision does not need to be large enough to accommodate screw extension connectors/towers and multiple screws can be inserted through the same skin incision.

The present invention does not just cover without continuous control of the screws but also includes "less" control than current methods. Current methods include large extension towers connecting from the screw heads to the skin surface and the present invention enables smaller connectors to the surface (and not just no connectors).

It would be appreciated by those skilled in the art that various changes and modifications can be made to the illustrated embodiments without departing from the spirit of the present invention. All such modifications and changes are intended to be within the scope of the present invention except as limited by the scope of the appended claims.

I claim:

1. A device comprising:
    a rod holder;
    a swivel arm pivotally attached to the rod holder;
    an inner stylet, a bottom portion of the inner stylet comprising a pincher to receive a rod;
    an outer sheath, the outer sheath configured to slide over the inner stylet;
    a T depressor configured to slide over an upper portion of the inner stylet; and
    a ratchet positioned on a top portion of the swivel arm, the ratchet configured to lock on to the T depressor.

2. The device of claim 1, wherein the outer sheath comprises ridges configured to fit into distal grooves in a lower portion of the swivel arm.

3. The device of claim 1, wherein the rod holder comprises a band configured to limit swivel of the swivel arm based on a rod length.

4. The device of claim 1, wherein the rod holder comprises a band configured to limit swivel of the swivel arm based on a rod length, and further comprising wherein the band comprises a screw to tighten a position of the swivel arm with respect to the rod holder.

5. The device of claim 1, wherein the rod holder comprises a band configured to limit swivel of the swivel arm based on a rod length, further comprising wherein the band comprises a screw to tighten a position of the swivel arm with respect to the rod holder, and wherein the band further comprises a handle.

6. The device of claim 1, wherein the inner stylet further comprises:
    ridges configured to secure above and below the T depressor; and
    screw threads configured to secure and tighten to the outer sheath.

7. The device of claim 1, wherein the outer sheath comprises:
    an upper section, the upper section including internal threads to mate with the screw threads of the inner stylet and small ridges to fit a locking wrench; and
    a lower section, the lower section including ridges to fit distal grooves in a lower portion of the swivel arm.

8. The device of claim 1, wherein the T depressor comprises:
    an insertion groove configured to slide through the inner stylet; and
    a beveled edge configured to lock into the swivel arm.

9. The device of claim 1, wherein the inner stylet further comprises an upper fixation point for a navigation tracker.

10. The device of claim 1, wherein the rod holder has at least one centrally located external fixation point for a rod holder navigation tracker.

11. The device of claim 1, wherein the swivel arm has at least one upper located external fixation point for a swivel arm navigation tracker.

12. A spine fixation system comprising:
- a rod holder/inserter including a rod guide member and a swivel arm pivotably connected to the rod guide member, wherein the rod guide member includes an opening dimensioned to receive the swivel arm therethrough, a distal end having an open back to receive a rod therethrough, and wherein the swivel arm includes a distal front opening dimensioned to receive the rod and having a solid distal base and back wall to secure the rod;
- an inner stylet including a pincher at its distal end having an opening configured to receive and retain the rod therein,
- a U-shaped T depressor including two arms defining an insertion groove therebetween and each arm having a beveled edge configured to lock into a portion of the swivel arm; and
- an outer sheath including a lower part and an upper part configured to cooperate with the lower part, the outer sheath including means for engaging the inner stylet.

13. The system of claim 12, further comprising a band connected to the swivel arm and configured to limit swiveling motion thereof.

14. The system of claim 12, further comprising a band connected to the swivel arm and configured to limit swiveling motion thereof, and wherein the band includes a screw to tighten a position of the swivel arm with respect to the rod guide member.

15. The system of claim 12, wherein the swivel arm includes distal grooves and wherein the lower part of the outer sheath includes ridges configured to insertably engage the distal grooves of the swivel arm.

16. The system of claim 12 wherein the inner stylet further comprises ridges configured to secure above and below the T depressor; and
threads configured to secure and tighten to the outer sheath.

17. The system of claim 12, wherein the outer sheath means for engaging the inner stylet includes an open proximal end of the upper part having internal threads configured to engage threads on the inner stylet.

18. The system of claim 12, wherein the swivel arm includes a ratchet at a proximal portion thereof, the ratchet configured to lock on to the T depressor.

19. The system of claim 12, wherein the rod guide member includes at least one external fixation point for a rod guide member navigation tracker and wherein the swivel arm includes at least one external fixation point for a swivel arm navigation tracker.

20. The system of claim 12, wherein the inner stylet includes an inner stylet navigation tracker at its proximal end.

* * * * *